(12) United States Patent
Aflatoon

(10) Patent No.: US 9,333,094 B2
(45) Date of Patent: May 10, 2016

(54) MINIMALLY INVASIVE EXPANDABLE INTERBODY FUSION CAGE

(71) Applicant: Kamran Aflatoon, Corona del Mar, CA (US)

(72) Inventor: Kamran Aflatoon, Corona del Mar, CA (US)

( * ) Notice: Subject to any disclaimer, the term of this patent is extended or adjusted under 35 U.S.C. 154(b) by 86 days.

(21) Appl. No.: 14/243,305

(22) Filed: Apr. 2, 2014

(65) Prior Publication Data

US 2015/0230936 A1 Aug. 20, 2015

Related U.S. Application Data

(63) Continuation-in-part of application No. 14/180,580, filed on Feb. 14, 2014.

(51) Int. Cl.
*A61F 2/44* (2006.01)
*A61F 2/28* (2006.01)
*A61F 2/30* (2006.01)

(52) U.S. Cl.
CPC ......... *A61F 2/447* (2013.01); *A61F 2002/2835* (2013.01); *A61F 2002/3038* (2013.01); *A61F 2002/30462* (2013.01); *A61F 2002/30579* (2013.01); *A61F 2002/30904* (2013.01); *A61F 2002/448* (2013.01)

(58) Field of Classification Search
USPC ............................................. 623/17.11–17.16
See application file for complete search history.

(56) References Cited

U.S. PATENT DOCUMENTS

| | | | |
|---|---|---|---|
| 9,084,637 B2 * | 7/2015 | Pasquet et al. | |
| 2005/0165486 A1 * | 7/2005 | Trieu | 623/17.13 |
| 2009/0270929 A1 * | 10/2009 | Suddaby | 606/324 |
| 2010/0185291 A1 * | 7/2010 | Jimenez et al. | 623/17.16 |
| 2010/0286783 A1 * | 11/2010 | Lechmann et al. | 623/17.12 |
| 2011/0009969 A1 * | 1/2011 | Puno | 623/17.12 |
| 2012/0259416 A1 * | 10/2012 | Blackwell et al. | 623/17.16 |
| 2013/0116791 A1 * | 5/2013 | Theofilos | 623/17.16 |
| 2013/0190876 A1 * | 7/2013 | Drochner et al. | 623/17.16 |
| 2013/0197642 A1 * | 8/2013 | Ernst | 623/17.16 |
| 2015/0012098 A1 * | 1/2015 | Eastlack et al. | 623/17.15 |

* cited by examiner

*Primary Examiner* — Jan Christopher Merene
(74) *Attorney, Agent, or Firm* — Ober, Kaler, Grimes & Shriver; Royal W. Craig

(57) ABSTRACT

An interbody fusion cage comprised of two support elements that separate after insertion into the interbody space to form a pocket into which graft material may be inserted. The expansion of the support elements deploys a band between the two support elements to further insulate the pocket into which the graft material is inserted, thereby holding it securely in place. The band may be formed of a flexible material so that it can fold to fit into a space between the support elements prior to separation of same.

15 Claims, 3 Drawing Sheets

MINIMALLY INVASIVE EXPANDABLE INTERBODY FUSION CAGE

CROSS-REFERENCE TO RELATED APPLICATIONS

The present application is a continuation in part of U.S. patent application Ser. No. 14/180,580 filed Feb. 14, 2014 which is incorporated herein by reference and which claims priority from U.S. patent application Ser. No. 13/892,724 filed May 13, 2013 which is also incorporated herein by reference.

BACKGROUND OF THE INVENTION

1. Field of the Invention

The present invention relates generally to devices and methods for treating spinal disorders and more specifically to an intervertebral device for aligning and maintaining the relative position of two or more adjacent vertebrae as well as to contain graft material to facilitate immobilization of the vertebra through fusion to eliminate the pain caused by abnormal motion.

2. Description of the Background

Degeneration of the intervertebral discs and the concomitant instability and translocation of the vertebra is a common cause of back pain and may result from a variety of problems including congenital deformity, age related degeneration, osteoporosis, tumor and disc herniation as a result of trauma. Disc degeneration, for whatever reason, results in compression of the spinal nerve roots resulting in pain. Palliative care is often successful in mild cases but more extreme or degenerative cases may require a surgical approach to stabilize the joint and relieve pressure.

A number of surgical approaches have been developed with varying degrees of success depending on the cause and severity of the damage. A ruptured disc impinging the nerve root may be partially excised to relieve pressure. In such a case the adjacent vertebra may be further fixated using rods, screws and plates in an attempt to stabilize the spine and delay or prevent further degeneration. Patients undergoing such excisions and fixations however, often require subsequent procedures to address recurrent pain. In many case such subsequent procedures include fusion. Spinal fusion, or spondylosyndesis, is a surgical technique used to combine two or more vertebrae utilizing supplementary bone graft tissue in conjunction with the body's natural osteoblastic processes to eliminate relative movement as a source of pain. A variety of approaches to fusion are available including posterior fusion, postero-lateral fusion and anterior or posterior interbody fusion.

In the more traditional posterior fusion approach, performed in conjunction with partial excision of the ruptured disc, growth is induced between the bony vertebral laminae to fix the position of the vertebra. In the postero-lateral fusion method bone growth is induced to join the transverse processes to prevent motion between the adjacent vertebrae. However, both posterior and postero-lateral fusion tend to cause bony overgrowth leading to nerve root compression and pain by spinal stenosis. This, coupled with other risks, limitations and disappointing fusion success rates have caused surgeons searching for alternate fusion means to develop interbody fusion techniques.

Interbody fusion techniques involve complete excision and replacement of the soft disc with autograft material harvested from the patient, prepared allograft from a donor source or, more recently, bone morphogenic protein. Most commonly performed in the lumbar region, the procedure can be accomplished from an anterior approach (Anterior Lumbar Interbody Fusion or ALIF) or a posterior approach (PLIF). In either case the procedure attempts to reconstruct the normal anatomic relationships between the bony and the neural structures and has many advantages. Specifically, weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

Successful fusion results in a contiguous growth of bone to create a solid mass that will unite the vertebra. When fusion graft material is first placed it is soft and movable and lacks cohesive strength and is therefore incapable of remaining in position or carrying any load without assistance. A variety of appliances have been developed that attempt to hold the vertebrae to be joined still relative to one another under normal spinal activity and daily stress in order to allow the fusion process to occur over the 18-24 month period generally required. Such appliances, often referred to as interbody cages, provide a mechanically rigid scaffold in which the graft material may be placed.

Cage designs vary widely but generally fall into three categories. Horizontal cylinders (1) are generally made from titanium and inserted by either the posterior or anterior approach into complimentary holes bored into the intervertebral space. They can be placed by open or minimally invasive techniques. U.S. Pat. No. 5,026,373 to Ray, et al. discloses a cage of this design that includes a perforated, threaded exterior surface that can be screwed into place between the vertebra and packed with bone material. Bone growth through the perforations and into the cancelous bone of the vertebra exposed by the insertion results in the desired fusion.

A second design is in the form of a vertical cylinder or ring (2). Often referred to as a Harms cage, vertically cylindrical cages are also usually made from titanium and can be cut to length as desired so as to span larger segments of the lumbar spine. End caps are employed to prevent subsidence into the cancelous bone although this design suffers, as a result, from a requirement that its central void be packed with graft material prior to insertion. Due to its sharp edges it is most commonly inserted by open techniques. U.S. Pat. No. 5,989,290 to Biedermann et al, et al. discloses a cage of this design.

A third design form is the open box cage (3). Constructed of carbon, titanium or bio-compatible non-metallic materials, this design can be formed for an anatomical fit or to recreate the normal lumbar lordosis. Openings in the box walls permit graft material contained therein to contact the vertebral bone. Some designs utilize a single large cage. Alternately, a pair of smaller cages is utilized which can be inserted posteriorly using minimally invasive techniques. U.S. Pat. No. 6,241,769 to Nicolson et al, et al. discloses a box form cage having a central void having an open top and bottom and a dovetail system for structurally attaching the device to the adjacent vertebra which are prepared by cutting cooperative channels into their surfaces.

Cages provide enhanced mechanical stability prior to fusion, maintain the intervertebral disc height and ultimately provide a high rate of successful fusion. The ideal cage should rigidly immobilize the spine in all directions, be strong enough to withstand repeated loadings, and have a modulus of elasticity similar to that of cortical bone. It should also be easy to insert by open or minimally invasive methods, resist subsidence, translation or retropulsion and be clinically effective. Cage designs further must balance the competing priorities of being small enough to be inserted through the incisions of minimally invasive techniques while also being large enough to fill a significant portion of the interbody space and present a significant area to the vertebral surface in which graft material can be inserted and retained to promote growth.

It would be therefore an improvement in this art to provide an interbody fusion cage for facilitating vertebral fusion and thereby eliminating spinal back pain caused by ruptured or degenerated vertebral discs which overcomes the deficiencies of prior known devices. Thus, it is an object of the present invention to provide an interbody fusion cage of open form design that can easily be placed in the evacuated interbody space to constrain relative vertebral motion and which can subsequently be secured again translation and retropulsion. It is a further object of the present invention to provide an interbody fusion cage that is sufficiently robust so as to withstand the forces imposed by normal daily activity on the part of the patient and which is clinically effective it retaining osteoconductive or osteoinductive material so as to facilitate fusion. It is a further object of the present invention to provide an interbody fusion cage that allows the surgeon easy access to the point of insertion of the graft material while providing maximum protection against graft material movement out of the interbody space.

SUMMARY OF THE INVENTION

Accordingly, there is provided an interbody fusion cage for insertion into the interbody space between adjacent vertebrae to promote fusion. The interbody fusion cage is comprised of two support elements that separate after insertion into the interbody space to form a pocket into which graft material may be inserted. The expansion of the support elements causes one or more flexible bands to extend between the two support elements to further enclose the pocket into which the graft material is inserted, thereby holding it securely in place. In a preferred embodiment, the band is constructed from a material that makes it strong enough to resist movement of the graft material within the pocket after insertion, and includes fenestrations along its length to increase its flexibility.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

DETAILED DESCRIPTION OF THE PREFERRED EMBODIMENTS

Figure 1:
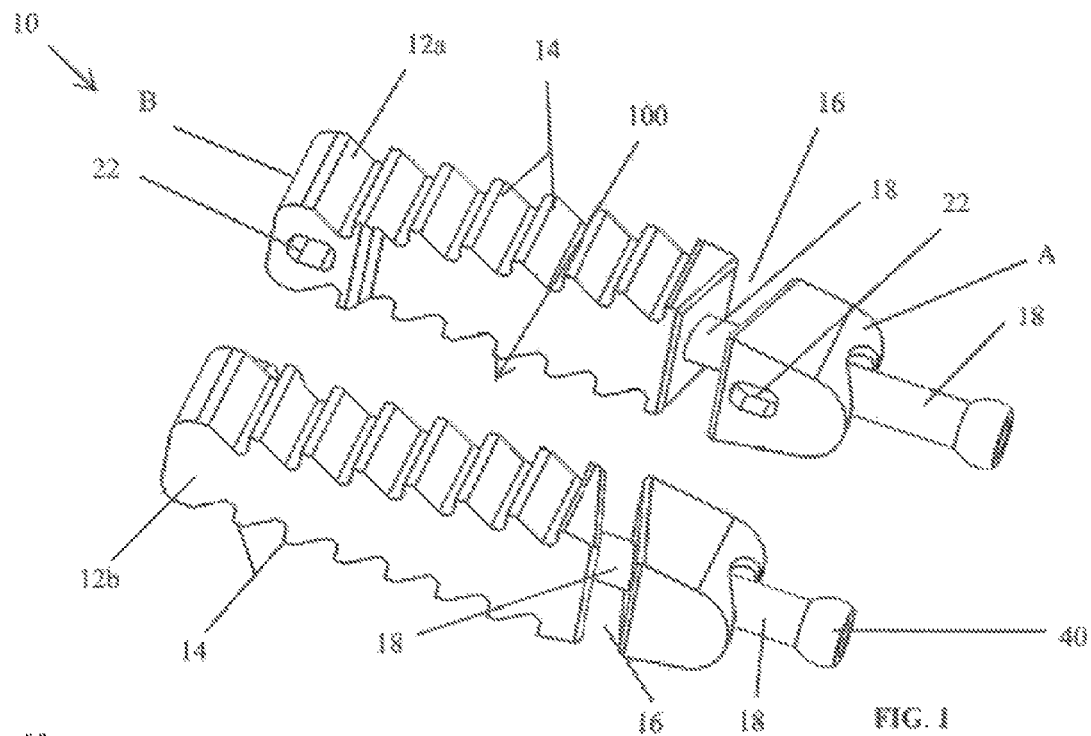
FIG. 1 is a perspective view of a partial embodiment according to the present invention from the side.

With reference to FIGS. 1 through 4, an interbody fusion cage 10 according to the present invention includes a main body consisting of two similarly-shaped support elements 12a and 12b. As shown in FIG. 1, support elements 12a, 12b are cooperatively formed, each preferably having a compact cross section and an elongate shape generally tapering to a front portion A from a back portion B to along the longitudinal axis to facilitate insertion of the cage 10 into the fully or partially evacuated interbody space of the patient through minimally invasive means. Opposing top and bottom portions along the elongate axis of support elements 12a and 12b are preferably textured with, for example, a multitude of ridges 14 for increased frictional engagement with the adjacent bone upon insertion of the cage 10 into the interbody space. Ridges 14 are preferably in the form of backwards-leaning teeth such that the cage 10 moves more easily in a frontal direction for insertion into the interbody space and less easily in a backwards direction to prevent the cage 10 from easily sliding out of the interbody space once inserted or during the insertion process. Ridges 14 may also take the form of grooves, knurling or other surface texture to increase friction with the adjacent bone after insertion of the cage 10 into the interbody space.

The length of the support elements 12a, 12b, as measured from the front portion A to the back portion B, is preferably from 35 mm to 60 mm and is selected by the surgeon depending on the physiology of the particular patient in which the cage 10 will be implanted. The height of the support elements 12a, 12b as measured between the opposing top and bottom portions containing ridges 14 is selected by the surgeon generally to replicate the natural height of the interbody space taking into account the thickness of the support elements 12a, 12b and anticipated subsidence during fusion. The height of the support elements 12a, 12b preferably decreases towards the front portion A of the support elements 12a, 12b as described above to facilitate insertion of the cage 10 into the interbody space whereby the cage 10 is inserted front first into the opening used to access the interbody space. The width of support elements 12a, 12b need only be large enough to accommodate pins 18 as described below. An exact width for support elements 12a, 12b may be dictated by physiology of the particular patient and/or the amount of weight that support elements 12a, 12b will be required to bear, etc.

Figure 2:
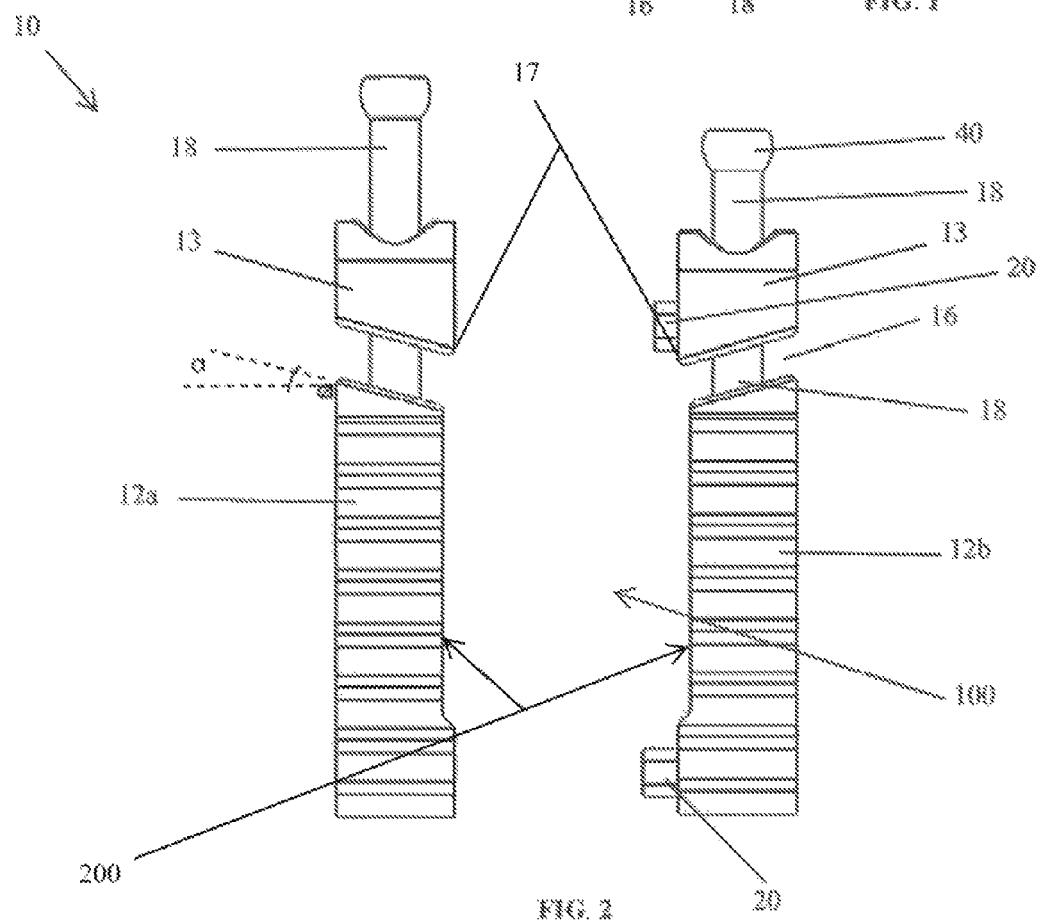
FIG. 2 is a top view of a partial embodiment according to the present invention.

Although cooperatively formed, the front portion A of each support element 12a, 12b includes a tip 13 separable from the remainder of the body forming the support elements 12a, 12b. Tip 13 joins the body of the supports elements at a preferably vertical, preferably planar joint 16. The term vertical as used herein refers to the direction perpendicular to the plane through the longitudinal axes of the two support elements 12a, 12b and is generally in the direction of the longitudinal axis of the spinal column of the patient when the device is implanted. In addition to being vertical, the plane of the joint 16 between the tip 13 and the remainder of the support elements 12a, 12b is preferably rotated an angle α from 10 to 45 degrees inward as depicted in FIG. 2. For purposes of this application, "inward" means in the direction of the opposing support element, and rotation of the plane of the joint "inward" means rotation such that the face of the end of a support element is turned toward the other support element. By way of example only, as depicted in FIG. 2, the face of the end of support element 12a is rotated inward by rotating angle α in a clockwise direction while the face of the end of support element 12b is rotated inward by rotating angle α in a counterclockwise direction.

With continued reference to FIGS. 1 through 4, the tips 13 at the front portion A of the support elements 12a, 12b are mechanically joined to the main body portion of the support elements, preferably by a pin 18. Pin 18 is most preferably a threaded screw with a low profile head 40 extending through the tips 13 and into the main body of the support elements 12a, 12b along its longitudinal axis. Advancement of pin 18 into the support element 12a, 12b serves to draw the tip 13 up to the support element 12a, 12b to capture a hand 24 as will, be described. As can be best seen in FIG. 4, the tips 13 are preferably slightly wider than the support elements 12a, 12b when viewed from above such that the inside edges of the tips 13 protrudes (inward) past the inside edge or surface 200 of the support elements 12a, 12b to form protrusions 17. Alternately, if not wider, the tips 13 may be affixed to the support elements in an offset manner so as to protrude inward as described. This protrusion 17 is preferably from 0.4 to 0.75 mm. A cooperatively formed and dimensioned protrusion 17 is provided on the inside surfaces 200 of the back portion B of the support elements 12a, 12b such that a minimum pocket 100 of 0.8 to 1.5 mm is maintained between the two support elements 12a, 12b when they are immediately adjacent to one another.

Figure 3:
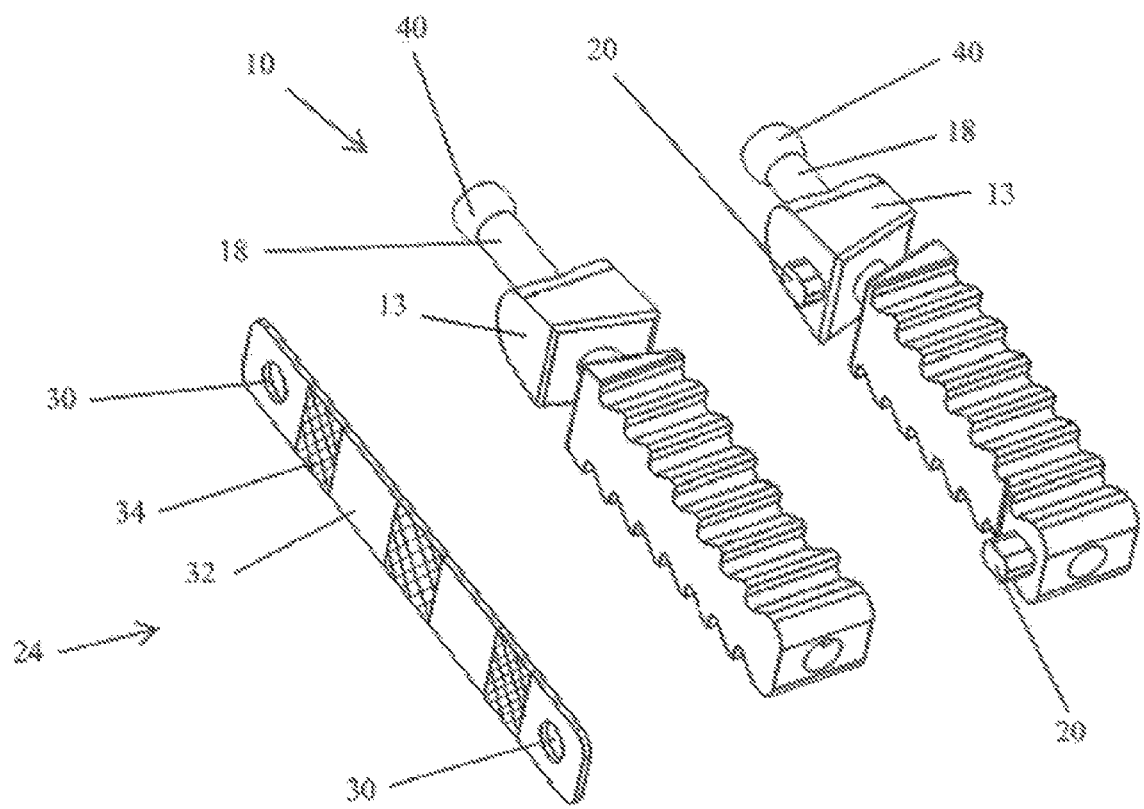
FIG. 3 is a perspective view of an embodiment according to the present invention from the back.
Figure 5:
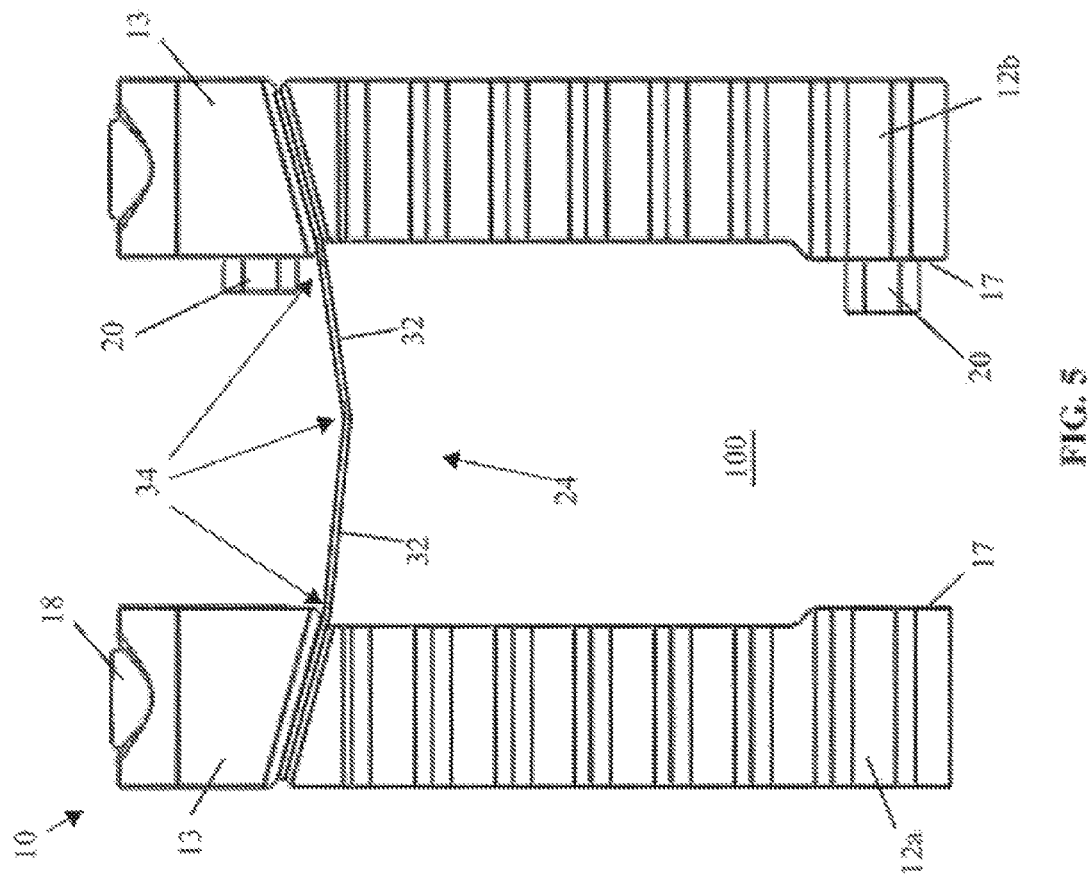
FIG. 5 is a top view of an embodiment according to the present invention in a deployed state.
Figure 4:
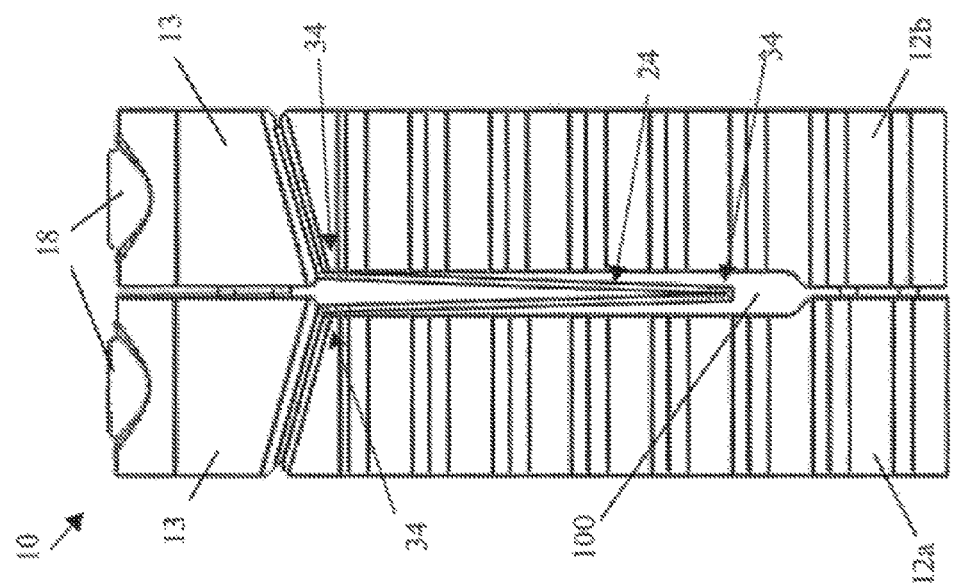
FIG. 4 is a top view of an embodiment according to the present invention in a stowed state.

With reference to FIGS. 3, 4 and 5, a flexible band, 24 is provided extending between the two support elements 12a, 12b. The band 24 is generally a flat planar element created from an elastically deformable material (i.e., spring-like) or, preferably, from a shape memory alloy such as Nitinol™. Band 24 may alternately be formed of a biocompatible polymer thin films such as polyetheretherketone (PEEK), polyethylenes (such as BoPET), polypropylene, polyphenylene (SRP), polycarbonate, polyphenylsulfone (PPSU), polysulfone (PSU) and Polyoxymethylene (POM) as well as silicone rubber sheets. Moreover, band 24 may be formed of any biocompatible material that is sufficiently flexible to be bent into a folded shape as further described below while simultaneously maintaining sufficient rigidity to contain graft material in pocket 100.

Band 24 is preferably an elongate structure having a height approximately equal to the height of support elements 12a, 12b. The length of band 24 may be determined as a design preference based on patient physiology or other considerations. More specifically, the length of band 24 is advantageously chosen to match the width of the interbody space into which cage 10 is to be inserted, because, as shown in FIG. 5, the length of band 24 will determine the maximum distance at which support elements 12a, 12b may be separated after insertion into the interbody space and thus the surface area that may be covered by pocket 100 that is formed from the separation thereof. The thickness of the band 24 may be from 0.1-0.4 mm and is preferably from 0.3-0.4 mm.

Band 24 is provided with holes 30 through its thickness at each end through which the pin 18 may be advanced so as to capture each end of the band 24 between a cap 13 and the body of a support element 12a, 12b. As depicted in FIG. 4, prior to its insertion into the interbody space the cage 10 is pre-assembled by removing the caps 13 and positioning an end of the band 24 before replacing the caps and inserting and advancing the pins 18 through the caps and the hole 30 to capture the ends of the band under the caps 13. In this pre-deployed state, the length of the band 24 is folded onto itself and stowed in the pocket 100 between the support elements 12a, 12b. In this pre-deployed state the support elements 12a and 12b are maintained in alignment by insertion of one or more protrusions or pegs 20 into cooperatively formed recesses 22 formed on or in the inside faces of the support elements 12a and 12b. In this way, relative vertical and for-ward-back motion of the support elements 12a and 12b is eliminated while lateral motion to separate the support elements 12a and 12b in the horizontal plane is permitted after implantation.

Importantly, bands 24 may be provided with multiple areas of fenestration 34 along their length spaced among portions of solid material 32. Where present, fenestrations 34 encompass the entire height and width of band 24 to facilitate and promote bending of the bands 24 along a vertical axis so as to permit stowing of the bands with the pocket 100 and subsequent deployment of the band 24. Fenestrations 34 are advantageously positioned in areas of band 24 where band 24 is required to flex in order to be stowed between the support elements 12a and 12b of the cage 10 in its pre-implantation, closed position, as shown in FIG. 4 (in which fenestrations 34 are depicted as cross hatching at bending portions of band 24). Fenestrations 34 allow those areas of band 24 that need to bend to fit into the closed cage 10 to do so, while the remainder of band 24 (at solid portions 32) advantageously maintains its rigidity to prevent graft material from slipping out of pocket 100 after placement. Fenestrations may be provided in the form of a series of piercings or perforations made through the thickness of the material from which the band 24 is constructed as by laser etching or other known process. Alternately, fenestrations may be made in the band 24 by cutting or otherwise forming a series of grooves in a first side of the band in the region to be fenestrated and thereafter cutting or otherwise forming a perpendicular series of grooves in a second side of the band in the region to be fenestrated such that the total depth of the two opposing series of grooves exceeds the thickness of the material thereby creating an opening through the band at the intersection of the opposing grooves. Thus, bands 24 may be formed from a solid sheet of Nitinol™ or other material and fenestrations 34 added thereafter.

Prior to insertion of the cage 10 into the patient's body, cage 10 is in a "closed" position wherein the side of support element 12a is in contact with the side of support element 12b, and more specifically, the protruding inside surfaces of the tips 13 and protrusions 17 are in contact with their respective counterparts at the front portion A or back portion B of the support element. As described, this compact arrangement produces a cage 10 with the smallest possible cross sectional area in order to facilitate the insertion of the cage 10 into the interbody space. In this configuration, once securely attached to support elements 12a, 12b by caps 13 and pins 18, band 24 resides in a folded position within the pocket 100 between support elements 12a, 12b, with fenestrations 34 facilitating this folded arrangement. Moreover, it should now be apparent that the angled design of the joint 16 between the caps 13 and body of the support elements facilitates positioning of the band 24 into the folded position between support elements 12a, 12b, as shown in FIG. 4.

After full or partial evacuation of the interbody space by the surgeon, cage 10 is inserted front portion A first into the interbody space through the opening made by the surgeon for evacuation of the same. Once the cage 10 has been satisfactorily positioned in the interbody space, the surgeon may utilize a tool, which may advantageously be integrated into the insertion tool used to insert the cage 10 into the interbody space, to move the cage 10 into the "open" position by laterally separating the support elements 12a and 12b. Upon opening of cage 10 the band 24 is deployed from its folded state between support elements 12a, 12b into a taught position extending between the now-separated support elements 12a, 12b. The support elements 12a, 12b are retained in their laterally separated deployed stare by engagement of the preferably ridged or otherwise articulated upper and lower surfaces with the bone of the adjacent superior and inferior vertebrae. Deployment of the band 24 clears it from the pocket 100 which is greatly enlarged so as to provide an area bounded on three sides in which bone graft material may be inserted and retained. In this way, cage 10 provides a relatively large pocket 100 for insertion of a large volume of graft material with a relatively compact cage 10 that can be inserted through a relatively small hole in its closed state, thus allowing for a minimally invasive operation. Cage 10 also provides a method for ALIF or PLIF without the necessity to load graft material into the cage prior to insertion into the interbody space.

The above-described embodiments provide a cage 10 that rigidly immobilizes the spine in all directions, is strong enough to withstand repeated loadings, and has a modulus of elasticity similar to that of cortical bone. The cage 10 as set forth in the above-described embodiments is also be easy to insert by open or minimally invasive methods because of its relatively compact design upon insertion in the closed position. Cage 10 thus balances the competing priorities of being small enough to be inserted through the incisions of minimally invasive techniques while also being large enough to fill a significant portion of the interbody space and present a significant area to the vertebral surface in which graft material can be inserted and retained to promote growth.

It should be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

I claim:

1. An interbody fusion cage for insertion between adjacent vertebra, comprising:
    a body portion comprising a pair of support elements each having a body and a cap fixedly affixed to an end of said body and combining therewith to form a contiguous upper surface and a contiguous lower surface joined by a contiguous inner surface and a contiguous outer surface, said inner surfaces each having two spaced protrusions from said body, said pair of support elements movable from a first position in which the two protrusions from the inner surface of the first support element are engaged to the two protrusions from the inner surface of the second support element so as to define a pocket between said first support element and said second support element wherein said inner surface of said first support element does not contact said inner surface of said second support element, and a second position in which said protrusions are disengaged;
    a band engaged at a first end to said first support element and engaged at a second end to said second support element, the portion of said band between said first end and said second end being folded within said pocket and sandwiched between said pair of support elements when said pair of support elements is in said first position;
    wherein said band is unfolded from said pocket and extends between said support elements upon movement of said support elements to said second position to define an area bordered by said support elements and said band in which to contain graft material.

2. The interbody fusion cage of claim 1 wherein said pocket is from 0.8 to 1.5 mm wide.

3. The interbody fusion cage of claim 1 wherein said first end of said band is engaged to said end of said first support element by capture under said cap of said first support element, and wherein said second end of said band is engaged to said end of said second support element by capture under said cap of said second support element.

4. The interbody fusion cage of claim 3 wherein said cap of said first support element is affixed to said end of said first support element by a first pin, and wherein said cap of said second support element is affixed to said end of said second support element by a second pin.

5. The interbody fusion cage of claim 4 wherein said first pin and said second pin are each a screw.

6. The interbody fusion cage of claim 3 wherein said cap of said first support element forms a first vertical plane of engagement with said end of said first support element and wherein said cap of said second support element forms a second vertical plane of engagement with said end of said second support element and wherein said first and second planes of engagement are each rotated inward from 10 to 45 degrees.

7. The interbody fusion cage of claim 6 wherein said first and second planes of engagement are each rotated inward from 15 to 25 degrees.

8. The interbody fusion cage of claim 3
    wherein said cap of said first support element is affixed to said first support element such that a side of said cap of said first support element protrudes inward beyond said inner surface of said first support element and engages said second support element when said pair of support elements is in said first position.

9. The interbody fusion cage of claim 8
    wherein said cap of said second support element is affixed to said second support element such that a side of said cap of said second support element protrudes inward beyond said inner surface of said second support element and engages said first cap when said pair of support elements is in said first position.

10. The interbody fusion cage of claim 1 wherein said band contains a plurality of fenestrated areas along its length to allow said band to bend into said folded position between said support elements.

11. The interbody fusion cage of claim 1 wherein said upper surfaces and said lower surfaces of said pair of support elements are each defined by a plurality of ridges.

12. The interbody fusion cage of claim 1 wherein said band is a flat planar element created from an elastically deformable material.

13. The interbody fusion cage of claim 1 wherein said band is a flat planar element created from a shape memory alloy.

14. The interbody fusion cage of claim 1 wherein said band has a thickness of between 0.1 mm and 0.4 mm.

15. The interbody fusion cage of claim 12 wherein said band has a thickness of between 0.3 mm and 0.4 mm.

* * * * *